(12) United States Patent
Hamel et al.

(10) Patent No.: US 8,638,191 B2
(45) Date of Patent: Jan. 28, 2014

(54) WIRELESS HAND-CONTROL OF DEVICE BY MEANS OF WIRELESS BUTTON

(75) Inventors: Andrew J. Hamel, San Mateo, CA (US); Brannon P. Wells, San Jose, CA (US); Reid S. Cover, Mountain View, CA (US); Michael G. Hilldoerfer, Sunnyvale, CA (US)

(73) Assignee: Stryker Corporation, Kalamazoo, MI (US)

( * ) Notice: Subject to any disclaimer, the term of this patent is extended or adjusted under 35 U.S.C. 154(b) by 1140 days.

(21) Appl. No.: 12/284,056

(22) Filed: Sep. 18, 2008

(65) Prior Publication Data

US 2009/0085718 A1 Apr. 2, 2009

Related U.S. Application Data

(60) Provisional application No. 60/997,024, filed on Sep. 28, 2007.

(51) Int. Cl.
*G05B 19/00* (2006.01)
*G05B 23/00* (2006.01)
*G08B 13/14* (2006.01)
*H04Q 5/22* (2006.01)
*A61B 17/00* (2006.01)
*A61B 17/04* (2006.01)
*A61B 18/04* (2006.01)
*A61B 17/32* (2006.01)
*A61B 1/00* (2006.01)
*A61B 1/267* (2006.01)

(52) U.S. Cl.
USPC ....... 340/5.5; 340/5.81; 340/572.1; 340/10.1; 340/10.33; 606/1; 606/147; 606/164; 606/170; 600/104; 600/133; 600/198

(58) Field of Classification Search
USPC .......... 340/572.1, 825.69, 825.72, 5.23, 457, 340/438, 825.24, 825.37, 5.22, 5.62, 5.72, 340/10.51, 693.9, 572.7; 235/385, 375, 235/383, 462.13; 713/153, 162, 169, 170; 606/1, 10, 2, 147, 34
See application file for complete search history.

(56) References Cited

U.S. PATENT DOCUMENTS

| 4,979,594 | A | | 12/1990 | Begle et al. |
| 5,838,223 | A | | 11/1998 | Gallant et al. |
| 6,133,833 | A | * | 10/2000 | Sidlauskas et al. ........ 340/572.1 |
| 6,274,829 | B1 | | 8/2001 | Rankin |
| 6,768,415 | B1 | | 7/2004 | Tuttle |

(Continued)

FOREIGN PATENT DOCUMENTS

WO  WO 2008034913 A2 * 3/2008

*Primary Examiner* — Jennifer Mehmood
*Assistant Examiner* — Mirza Alam
(74) *Attorney, Agent, or Firm* — Flynn, Thiel, Boutell & Tanis, P.C.

(57) ABSTRACT

A system for providing wireless remote control over one or more devices. Included in the system is at least one wireless button that can be placed at various locations and which communicates with at least one sensor when the wireless button and sensor are brought within close proximity to one another. According to one embodiment, a wireless button can only be activated when the button is located within an authorized activation area. In another embodiment, a wireless button can only be activated by an authorized user. In yet a further embodiment, a wireless button can only be activated by an authorized user when the button is located within an authorized activation area.

21 Claims, 9 Drawing Sheets

(56) References Cited

U.S. PATENT DOCUMENTS

| | | |
|---|---|---|
| 6,933,655 B2 | 8/2005 | Morrison et al. |
| 7,002,483 B2 | 2/2006 | Alrabady |
| 2002/0171559 A1* | 11/2002 | Yang ........................ 340/825.69 |
| 2003/0093103 A1* | 5/2003 | Malackowski et al. ....... 606/170 |
| 2006/0129140 A1* | 6/2006 | Todd et al. ........................ 606/1 |
| 2006/0161054 A1* | 7/2006 | Reuss et al. .................... 600/300 |
| 2007/0027459 A1* | 2/2007 | Horvath et al. ................ 606/147 |
| 2008/0006696 A1* | 1/2008 | Piersol et al. .................. 235/451 |
| 2008/0167522 A1* | 7/2008 | Giordano et al. ............. 600/104 |
| 2008/0314973 A1* | 12/2008 | Zuhars et al. .................. 235/380 |

\* cited by examiner

WIRELESS HAND-CONTROL OF DEVICE BY MEANS OF WIRELESS BUTTON

CROSS-REFERENCE TO RELATED APPLICATION

This application claims the benefit of U.S. Provisional Application No. 60/997,024, filed Sep. 28, 2007.

FIELD OF THE INVENTION

The present invention relates to a system for providing remote control to a device, and, more specifically, a system of wireless buttons that can be configured to provide secure remote control of the device in a multitude of locations.

BACKGROUND OF THE INVENTION

Many devices utilized in a medical or surgical environment do not include the capability to be controlled from a distance by means of a remote controller. Other devices may not offer remote hand-control, instead only having remote controls that are designed to be operated by foot. Some devices only provide remote controls that require the running of wires or cables, which precludes the use of the remote control within a sterile field of an operating room. Additionally, some remote controllers may simply not be configured in a manner preferred by a user.

Accordingly, what is needed is a system that allows a user to remotely control a device that otherwise offers no such capability, or allows a user to add hand-control to a device configured to be controlled only by foot. Also desired is a system that provides the ability for a user to create custom remote controls that can potentially be disposable.

SUMMARY OF THE INVENTION

A system for wirelessly remotely controlling one or more devices by means of at least one wireless button capable of being configured to control one or more functions of a remotely-located device. At least one sensor wirelessly detects activation of a button and signals a central control unit, which in turn will generate one or more control signals for controlling a device. According to one embodiment, a wireless button can only be activated by an authorized user. In another embodiment, a wireless button can only be activated when the button is located within an authorized activation area. In yet a further embodiment, a wireless button can only be activated by an authorized user when the button is located within an authorized activation area.

BRIEF DESCRIPTION OF THE DRAWINGS

One or more embodiments of the present invention are illustrated by way of example and should not be construed as being limited to the specific embodiments depicted in the accompanying drawings, in which like references indicate similar elements and in which.

DETAILED DESCRIPTION

Figure 1:
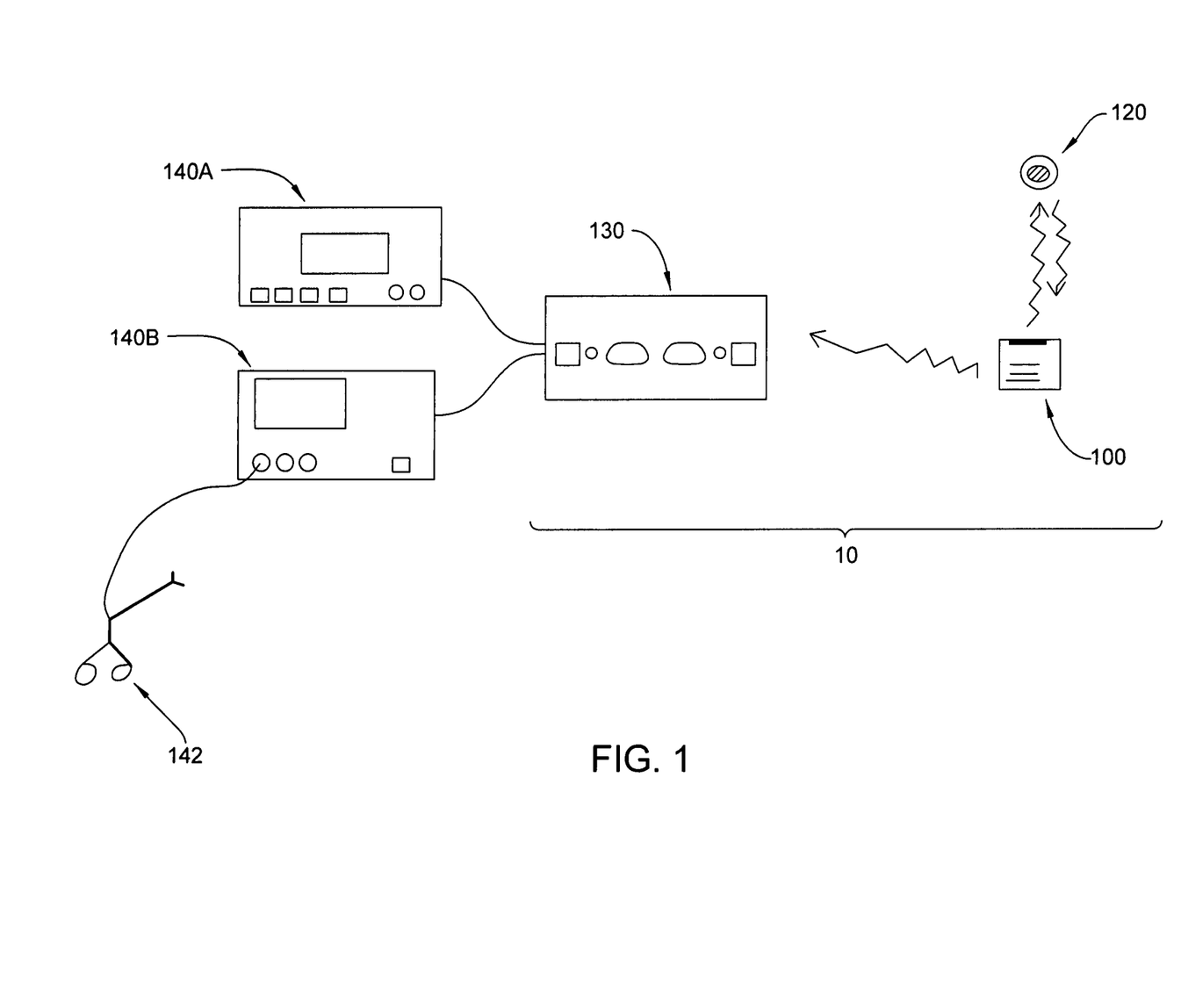
FIG. 1 illustrates a wireless button system according to one embodiment.

FIG. 1 depicts a wireless button system 10 that allows for the creation of a button interface capable of controlling one or more functions of one or more remote devices. The system 10 can be utilized to create hand-control of devices that otherwise are not configured to be controlled by hand, and allows for the establishment of button control in a location where such control does not exist (e.g., a location that, due to its position, is difficult to directly wire).

According to one embodiment as depicted in FIG. 1, the system 10 comprises at least one sensor 100, at least one wireless switch or button 120 (hereafter referred to simply as "button") and a central control unit 130. Connected to the central control unit 130 are one or more devices 140A, 140B for which remote control is desired. The devices 140A, 140B can vary in type and purpose as long as they are capable of receiving remote command signals issued by the central controller 130. Thus, for example, in the illustrated embodiment of FIG. 1, device 140A may be designed to control one or more lights located in an operating room, while device 140B is a surgical console for controlling a laparoscopic handpiece 142.

As will be discussed in greater detail below, sensor 100 is configured to wirelessly detect the activation of button 120. Upon detection of such activation, sensor 100 transmits, by either wireless or wired means, a signal that identifies button 120 to central control unit 130. In response to receiving the signal from sensor 100, central control unit 130 generates one or more control signals that have been previously associated with button 120 and forwards these one or more control signals to the appropriate device(s) 140A, 140B that is to be controlled.

As will be elaborated on in further detail in the discussion of the specific embodiments below, the sensor 100 is configured to wirelessly detect activation of button 120. According to one embodiment, button 120 may be any type of pushbutton that involves the occurrence of a mechanical/electrical interaction to turn on or off circuitry. Alternatively, button 120 may not actually be a pushbutton in the sense that a mechanical/electrical interaction occurs to enable or disable circuitry. Instead, button 120 may be detected by various means such as by proximity, with an actual button provided for tactile feedback or simply to provide a visual target. For example, in one embodiment, button 120 comprises a Radio Frequency Identification Device (RFID) tag, while sensor 100 comprises a RFID reader capable of detecting the RFID tag when brought into close proximity to a button 120. Alternatively, sensor 100 and button 120 may comprise some other form of inductive coil detection means. In yet another embodiment, sensor 100 may comprise an optical sensor configured to detect button 120 when brought into close proximity by detecting, for example, a color or texture of the button 120.

According to one embodiment of the present invention, activation of a wireless button is detected by means of a sensor located on a person. The sensor identifies the user of the device and allows that specific user to activate the wireless button. If a user does not possess the sensor, he or she would be unable to activate the wireless button.

Figure 2:
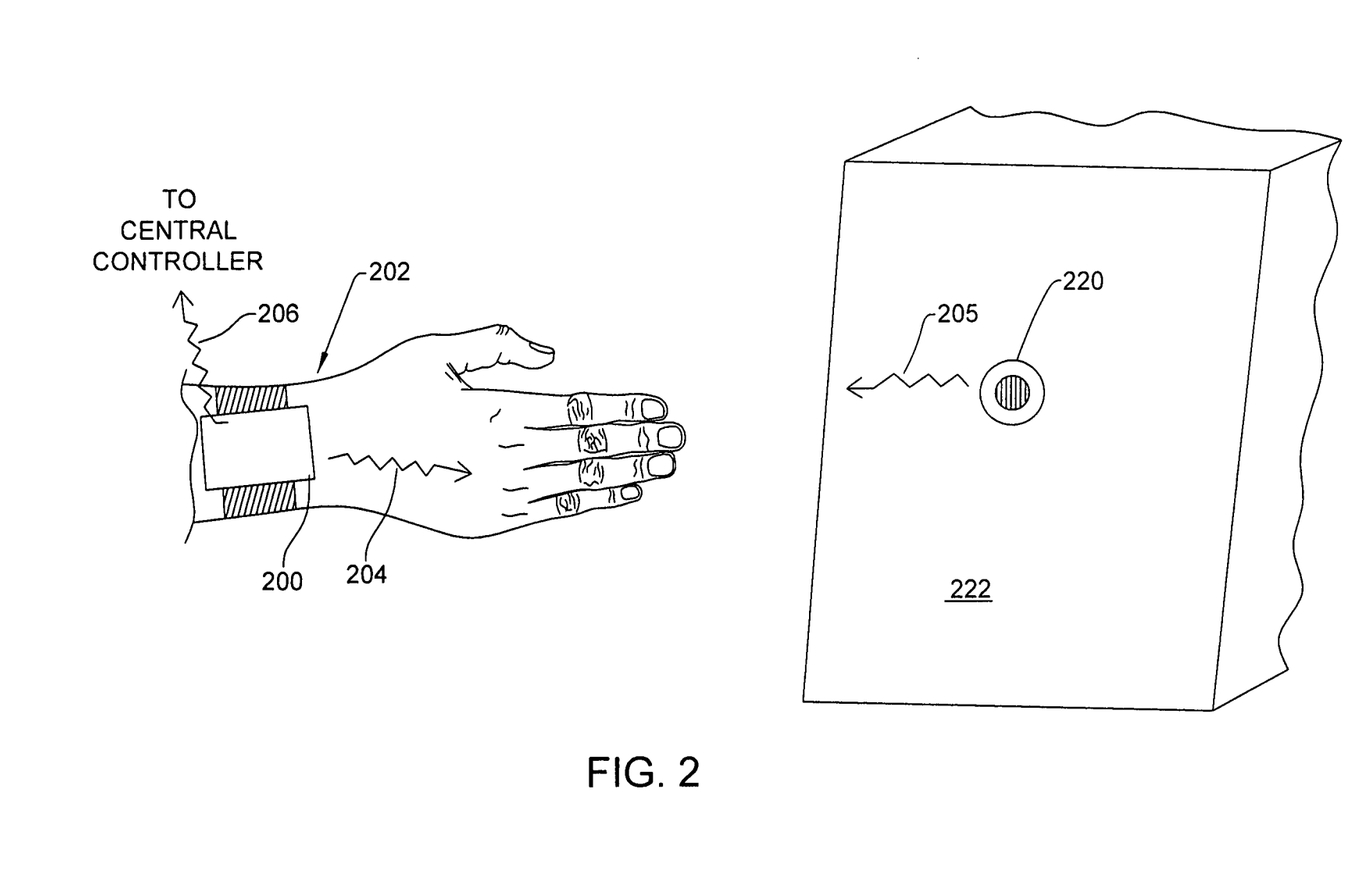
FIG. 2 illustrates a wireless button system according to another wherein the button can only be activated by an authorized user.

FIG. 2 depicts one embodiment where a portable sensor unit 200 is strapped to the wrist 202 of a user in a manner similar to a wrist watch. A wireless button 220 is attached to the surface of a structure 222, such as, for example, the wall of a room, or a structure within the room such as a fixture, piece of furniture, or device within the room. As previously discussed, the portable sensor unit 200 may comprise a RFID reader, while the wireless button comprises a RFID tag. When the user in possession of portable sensor unit 200 proceeds to touch or depress button 220 with their finger, the sensor unit 200 is placed within close proximity to the button 220. A wireless signal 204 transmitted by sensor unit 200 reaches button 220 when the sensor 200 and button 220 are in close enough proximity. Upon receiving the wireless signal 204, the RFID tag within button 220 transmits a wireless signal 205 back to the sensor 200. The RFID reader within the sensor unit 200 detects the wireless signal 205, and in response, wirelessly transmits to the central control unit (see FIG. 1) a signal 206 that identifies the status of the button 220 that was just activated by the user.

In the above embodiment, any person not in possession of a sensor 200 is incapable of activating button 220, and thus cannot use the button 220 as a wireless remote control. Accordingly, the wireless button system not only allows for the creation of a wireless remote control where one did not exist before, but also provides a level of security wherein a unauthorized user cannot remotely control a device as they are unable to activate button 220.

Figure 3:
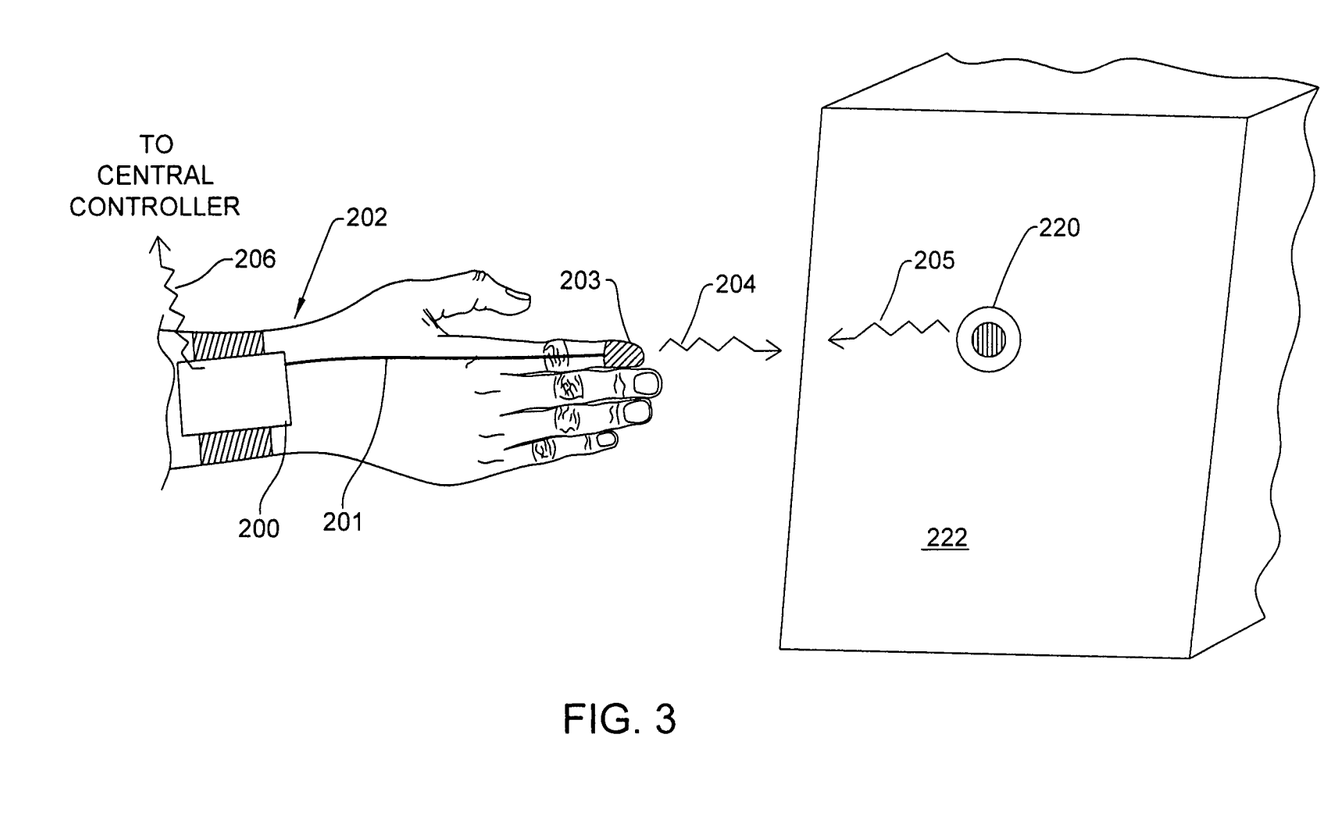
FIG. 3 illustrates a wireless button system that utilizes a finger cover.

In the embodiment depicted in FIG. 3, a portable sensor unit 200, designed to be worn upon the wrist 202 of a user, further comprises a finger cover 203 that is placed over one or more fingers of the user. The finger cover 203 contains the actual sensor (e.g., inductive coil) that is capable of detecting activation of button 220. Specifically, upon the user activating button 220, finger cover 203 is brought within close proximity to button 220. Similar to the previous embodiment, a wireless signal 204 being transmitted by the coil within finger cover 203 is received by button 220. In response, button 220 transmits a return wireless signal 205, which is received by the coil within finger cover 203 and subsequently relayed back to the sensor unit 200 by means of a wired connection 201. The sensor unit 200 then wirelessly transmits to the central control unit a signal 206 that identifies the status of the button 220.

Figure 4:
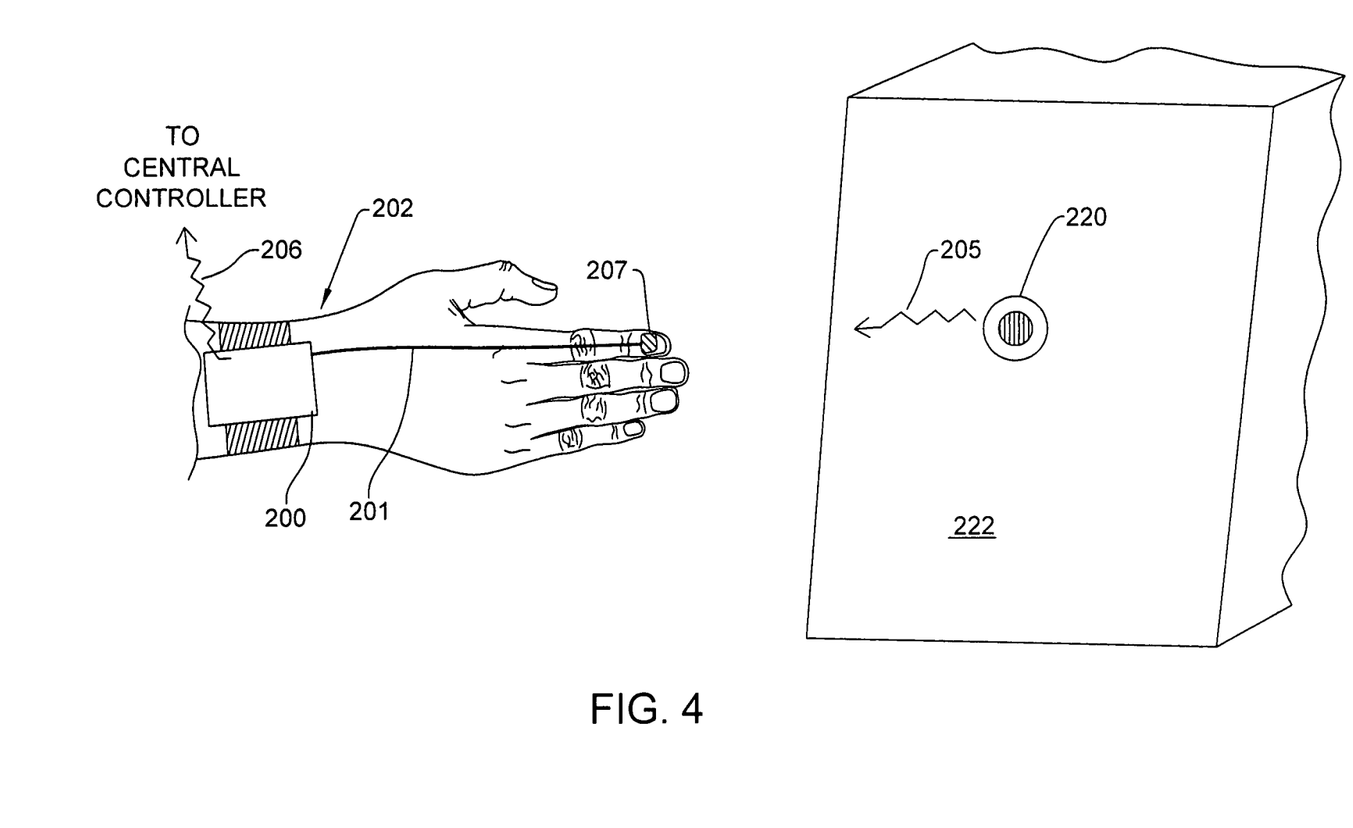
FIG. 4 illustrates a wireless button system that utilizes a sticker that is placed on the back of a finger of a user.

FIG. 4 illustrates an additional embodiment of the present invention that is similar to the embodiment of FIG. 3. As before, a sensor unit 200 is worn upon the wrist 202 of a user in a manner much like a wristwatch. However, instead of a finger cover, the sensor unit 200 of the current embodiment further comprises a sticker 207 that is placed upon the user's finger. The sticker 207 contains the actual sensor (e.g., coil) which detects the button 220 and subsequently communicates this information back to sensor unit 200 by means of wired connection 201.

In the embodiments of FIG. 3 and FIG. 4, the finger cover 203 or sticker 207, as well as the wired connection 201, can be configured to be disposable. Such a design facilitates the use of the wireless button system in a sterile environment such as that found in an operating room. The finger cover 203, sticker 207 and wired connection 201 can be manufactured to be sterile, and thus capable of being used within the defined sterile field of an operating room. Once these components are used, they can simply be disposed of and replaced with new sterile components.

According to another embodiment (not illustrated), the sensor unit 200 can be incorporated into a glove that can be worn upon the hand of the user. Integrated into the glove is a RFID reader or an inductive coil sensor, or alternatively, an optical sensor capable of detecting activation of button 220 by detecting a color or texture of the button 220 when the glove and button are brought into close proximity with one another.

In one embodiment, a sensor unit is not carried upon the body of a user, but instead is physically placed at a location that is in proximity to a defined area of activation. When a wireless button is located outside the defined area of activation, the button is not within close proximity to the sensor, and thus cannot be activated. However, if the button is repositioned so as to be within the defined area of activation, the sensor detects that the wireless button is in proximity and can thus detect the activation of the button and communicate such information back to the central control unit.

Figure 5:
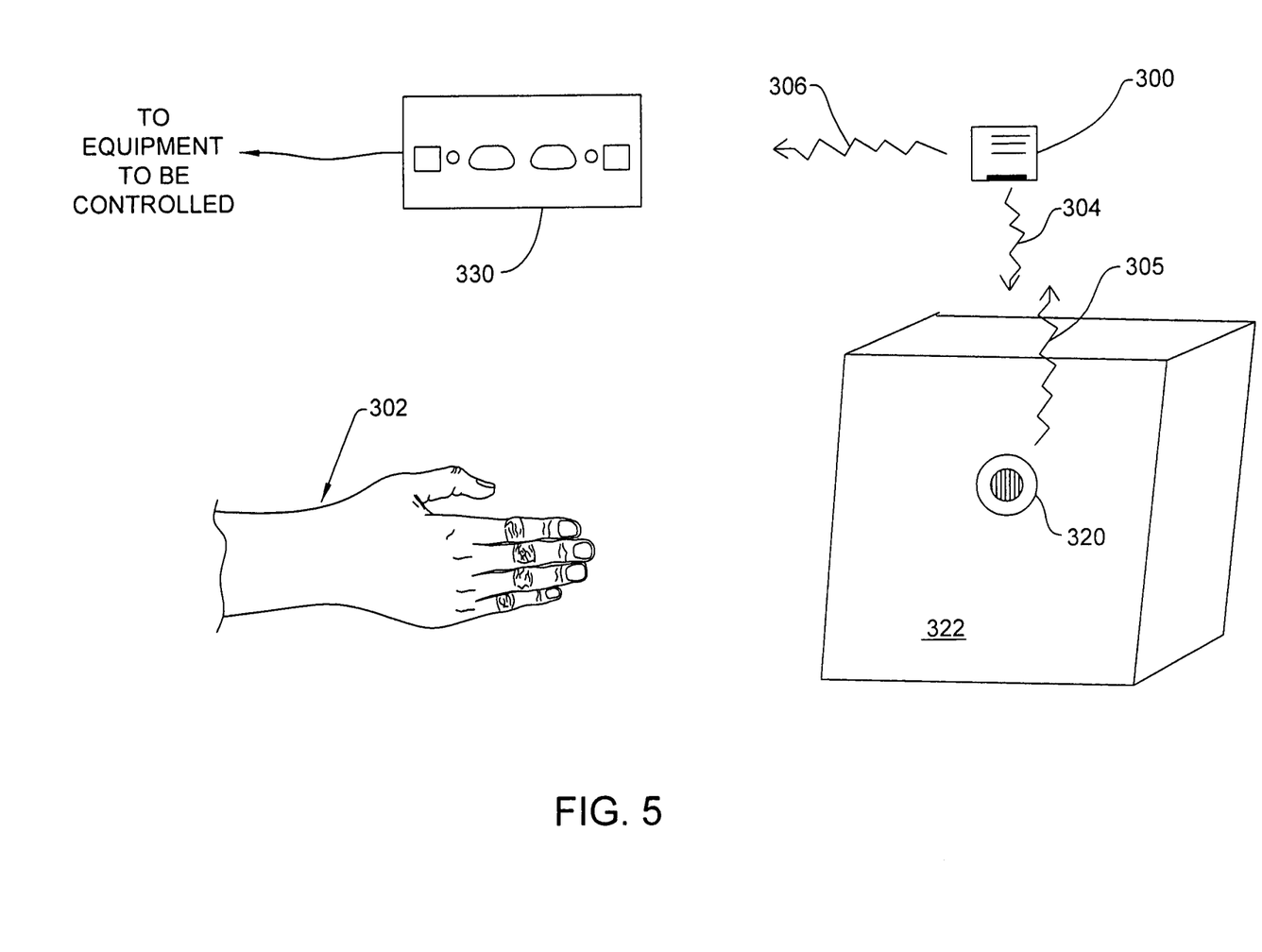
FIG. 5 illustrates a wireless button system that can only be activated when the button is located in an authorized activation area.

FIG. 5 illustrates one embodiment where an external sensor unit is positioned so as to define an area of activation. Similar to previous embodiments, a wireless button 320 is attached to the surface of a structure 322, such as, for example, a medical device or a movable cart supporting such a medical device. A sensor unit 300 is then positioned at a specific location so as to define an area where activation of the button 320 is permitted. Additionally present is a central control unit 330 that connects to and is capable of controlling one or more devices located in the area.

When the wireless button 320 is not located within a defined proximity of the sensor unit 300, it is not possible for a user 302 to activate the button 320. However, if the wireless button 320 is relocated so as to be in proximity to the sensor unit 300, then the wireless button 320 is capable of being activated by a user 302.

Specifically, the external sensor unit 300 can be configured into a variety of shapes and sizes, and can contain an inductive coil with a RFID reader. The wireless button 320 includes a RFID tag that normally resides in an inoperative state. When the button 320 is pressed by a user 302, a circuit within the button 320 is placed into a closed or completed state. This places the RFID tag into an operative state that is capable of receiving a wireless signal 304 transmitted by the sensor unit 300. Upon receipt of wireless signal 304, the RFID tag within the button 320 responds by transmitting a wireless signal 305 back to the sensor unit 300. The sensor unit 300 detects the wireless signal 305, and in response, transmits either a wired or wireless signal 306 to the central control unit 330 indicating that the button 320 has been pressed or activated. As in previous embodiments, the central control unit 330 then generates one or more corresponding control signals associated with wireless button 320 and forwards these one or more control signals to the appropriate device(s) that can be controlled.

In the above embodiment, the sensor unit 300 can be located above the desired area of activation, such as, for example, in the ceiling. To define an area of activation in an operating room, the sensor unit 300 can be located on the booms or lights above the surgery site, or alternatively, on the bed or on the patient. The sensor unit 300 can be configured so as to be permanently mounted at a location, or alternatively, be displaceable amongst various locations. Depending on whether the system is intended to be used in an operating room, the sensor unit 300 can be configured so as to be sterilizable, or manufactured to be an initially sterile, disposable unit.

Figure 6:
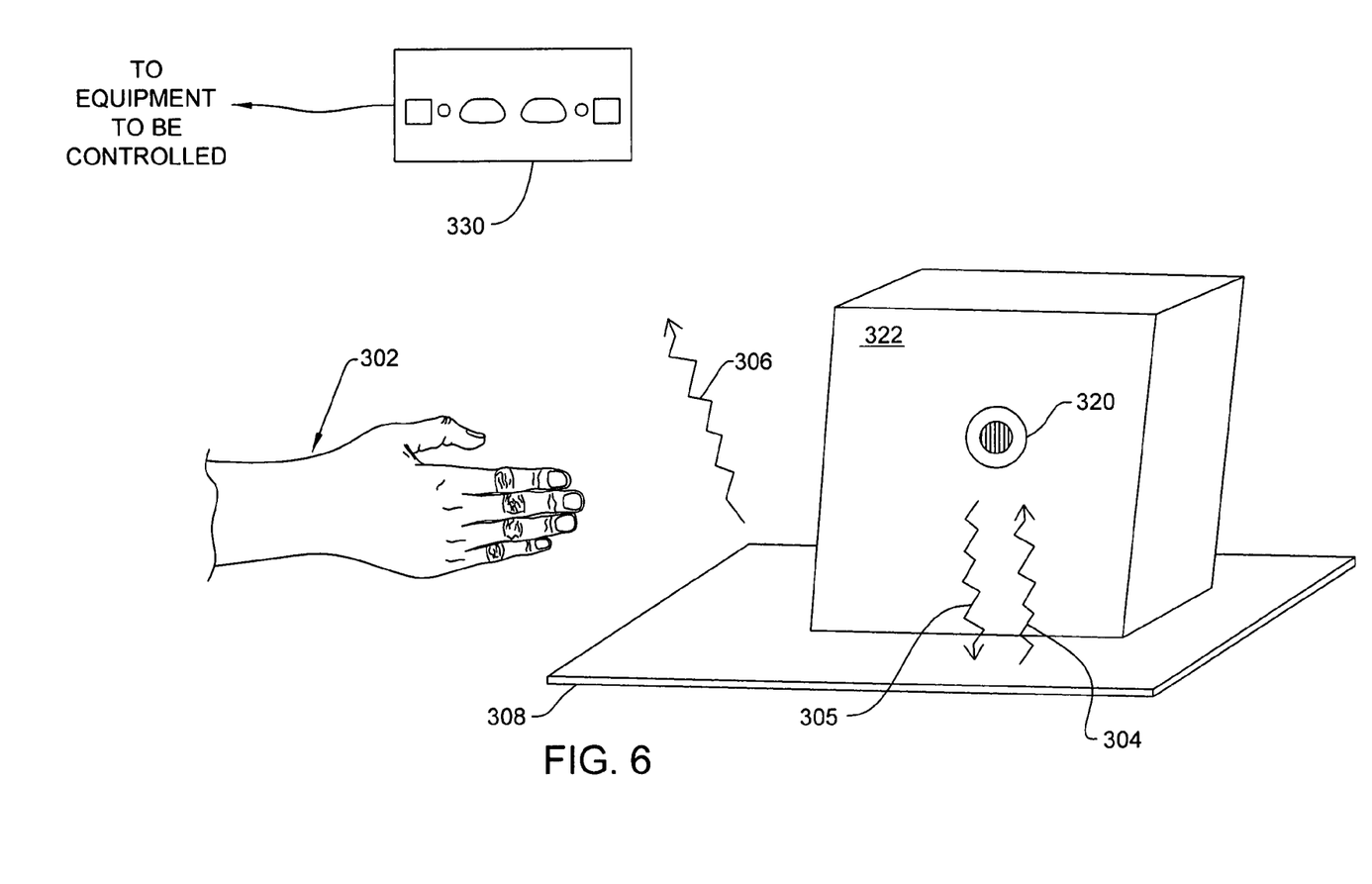
FIG. 6 illustrates a wireless button system that functions in a manner similar to the system of FIG. 5.

According to a further embodiment, the sensor unit 300 can be configured in the form of a pad or sheet that can be placed on a table or surface that is near the area of interaction between the wireless button 320 and a user 302. FIG. 6 illustrates one such example where the sensor unit is in the form of a sheet or pad 308. A user 302 can subsequently activate wireless button 320 once the structure 322, upon which the wireless button 320 is attached, is brought into close proximity to the sheet or pad 308.

It should be noted that unlike the embodiments depicted in FIGS. 2-4, the embodiments disclosed above with respect to FIGS. 5 and 6 do not distinguish authorized users from unauthorized users. Accordingly, any user is capable of activating the button 320 if the button is positioned so as to be within close proximity to the sensor unit 300.

In another embodiment of the present invention, a wireless button can be activated only when the button is in close proximity to a sensor unit and only when the person attempting to activate the button is an authorized user.

Figure 7:
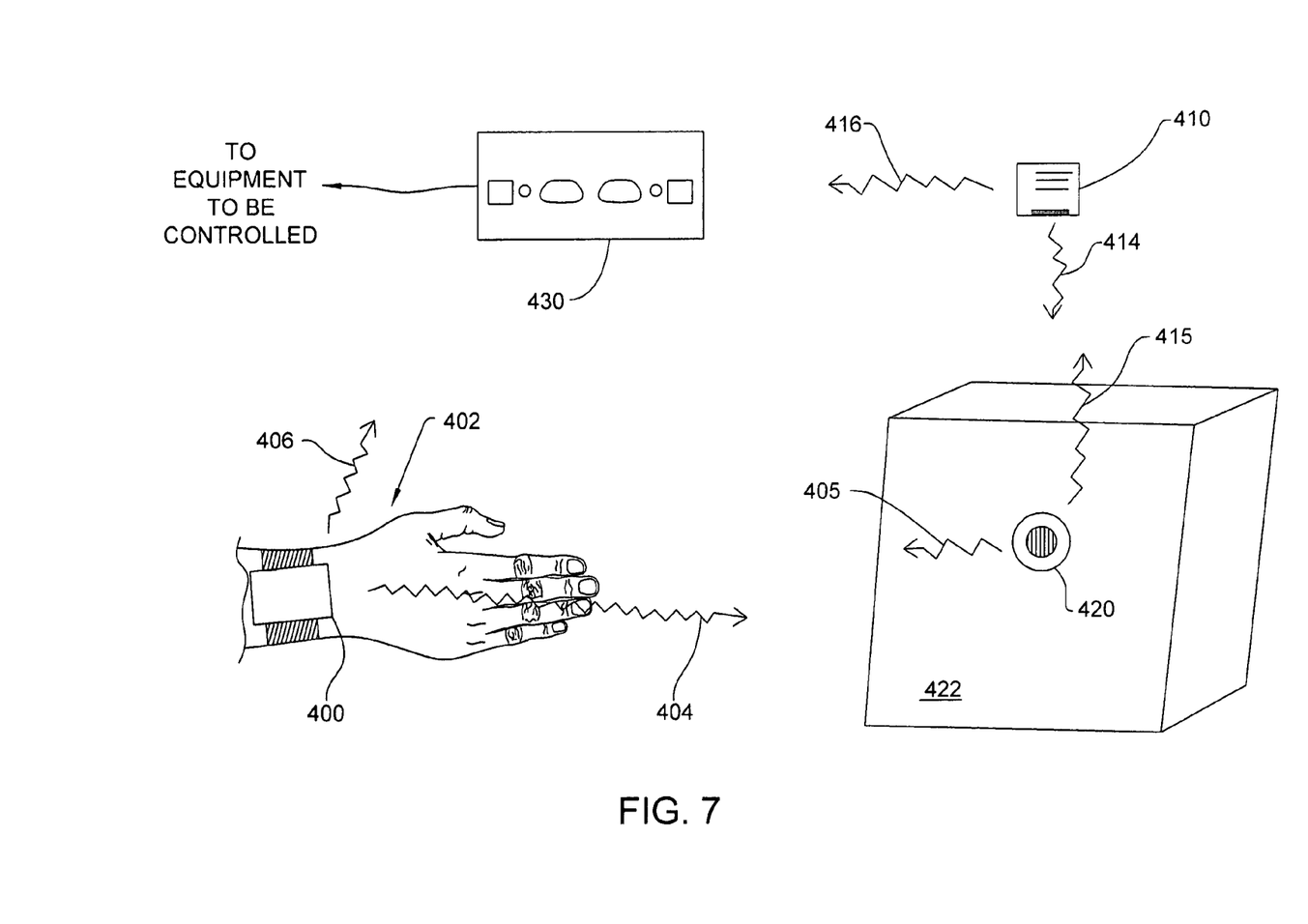
FIG. 7 illustrates a wireless button system according to one embodiment wherein the button can only be activated by an authorized user when the button is located in an authorized activation area.

As illustrated in FIG. 7, a wireless button 420 is attached to the surface of a structure 422, such as a fixture, piece of furniture, or device within the room. A first sensor unit 400 is carried on the body of a user 402, such as, for example, strapped to the wrist of the user 402. A second sensor unit 410 is positioned at a specific location so as to define a desired area of activation. Two separate criteria must be simultaneously met in order for the button 420 to be activated, and thereby cause the central control unit 430 to generate and forward one or more control signals on to one or more attached devices.

First, the button 420 must be in close proximity to sensor unit 410. Similar to the embodiments of FIGS. 5 and 6, sensor unit 410 transmits a wireless signal 414. If button 420 is in close proximity to sensor unit 410, button 420 will detect signal 414 and transmit back a wireless signal 415 that identifies the button 420. Upon receiving signal 415, sensor unit 410 transmits a signal 416 to central control unit 430 that indicates the activation state of button 420.

Second, the button 420 must be activated by an authorized user that is in possession of sensor unit 400. Similar to the embodiments of FIGS. 2-4, when an authorized user proceeds to touch or depress button 420, the sensor unit 400 is placed within close proximity to the button 420. A wireless signal 404 transmitted by sensor unit 400 is detected by button 420. In response, button 420 transmits a wireless signal 405 back to the sensor unit 400. In response to detecting wireless signal 405, the sensor unit 400 wirelessly transmits to the central control unit 430 a signal 406 that identifies the status of the button 420 that was just activated by the user.

Upon receiving both signal 406 and signal 416, thereby indicating that the button 420 was activated by an authorized user while the button 420 is in a defined activation area, central control unit 430 will proceed to generate one or more control signals associated with button 420 and forward those signals to the appropriate devices.

If the central control unit 430 only receives signal 406 indicating that an authorized user activated button 420, no action is taken as the button 420 is presumed to be located outside of the defined area wherein activation is allowed. Similarly, if the central control unit only receives signal 416 indicating that button 420 was activated while within close proximity to sensor unit 410, no action is taken as the button 420 is presumed to have been activated by an unauthorized user.

Figure 8:
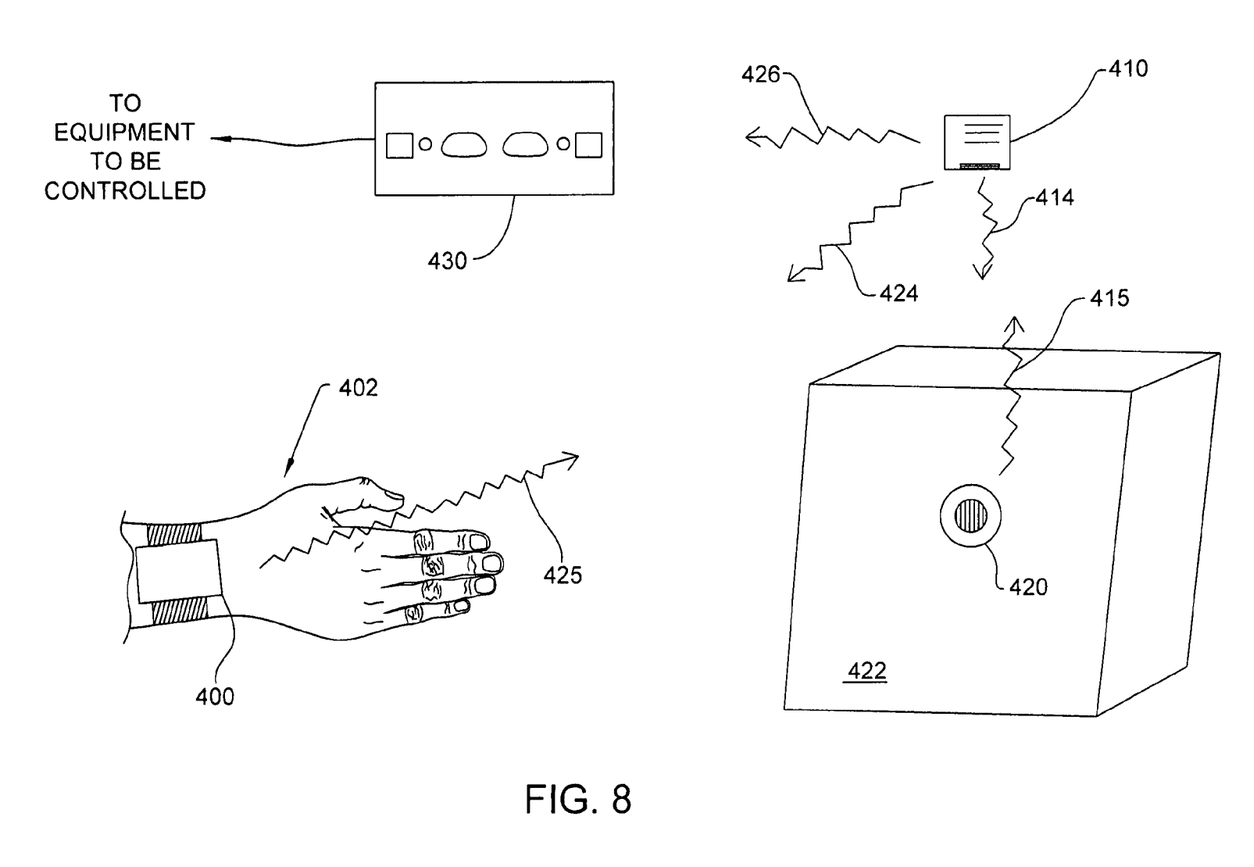
FIG. 8 illustrates a wireless button system according to another embodiment wherein the button can only be activated by an authorized user when the button is located in an authorized activation area.

FIG. 8 illustrates a similar embodiment to that of FIG. 7. However, according to this embodiment, central control unit 430 acknowledges authorized activation of a wireless button 420 upon receipt of a single signal 426 transmitted by sensor unit 410. As will be discussed in greater detail below, sensor unit 400 of the current embodiment, which is in the possession of an authorized user, does not communicate with central control unit 430, but instead communicates with sensor unit 410.

Specifically, when wireless button 420 is activated while in close proximity to sensor unit 410, the button 420 detects a wireless signal 414 transmitted by sensor unit 410. In response, button 420 wirelessly transmits a signal 415 back to sensor unit 410. At the same time, the sensor unit 400 in the possession of the authorized user 402 detects a wireless signal 424 that is also transmitted by sensor unit 410. In response, sensor unit 400 wirelessly transmits a signal 425 back to sensor unit 410.

Upon receiving both signal 415 and signal 425, thereby indicating that the button 420 was activated by an authorized user while the button 420 is in a defined activation area, sensor unit 410 will proceed to transmit to the central control unit 430 a signal 426 that identifies the status of the button 420 that was just activated. Thus, unlike the embodiment of FIG. 7, the determination of whether both button activation criteria are satisfied is carried out by sensor unit 410 instead of central control unit 430.

In the embodiments above, sensor unit 410 transmits a first signal 414 to wireless button 420 and transmits a second signal 424 to sensor unit 400. However, according to a further embodiment, signal 414 and signal 424 are the same signal. As a result, wireless button 420 and sensor unit 400 both detect the same signal and respond by transmitting signal 415 and signal 425, respectively.

Based on the plurality of embodiments above, the present invention is seen to disclose a system that allows for the remote control of at least one device through the use of one or more wireless buttons that can be placed in a variety of locations. Furthermore, the system provides for multiple layers of security that can prevent the remote control of a device if a button is located outside an authorized activation area, as well as prevent remote control of a device by an unauthorized user.

Applications for the wireless button system are numerous. According to one application, several wireless buttons can be used to create a customizable and potentially disposable remote control. For example, the system can be configured so that first, second and third buttons control first, second and third devices, respectfully. To aid a user in distinguishing one button from another, the buttons can be configured to have different colors and/or different shapes or designs.

Figure 9:
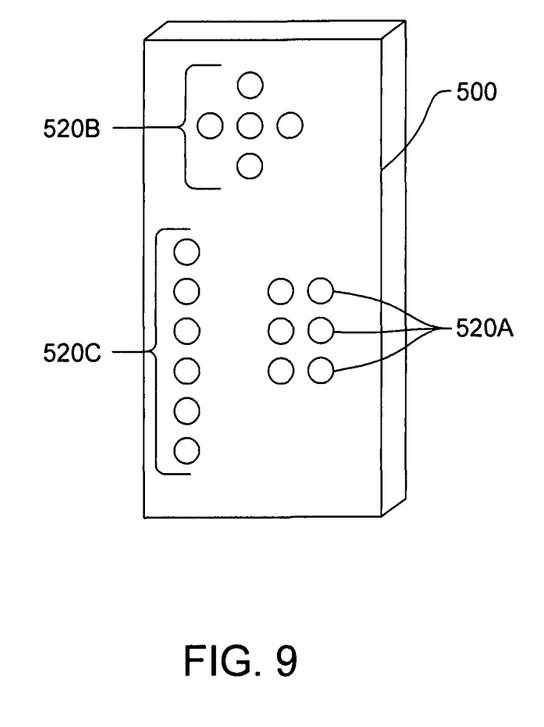
FIG. 9 illustrates one example of how a plurality of wireless buttons can be utilized.

FIG. 9 illustrates one example of a customized remote control created by the placement of a plurality of wireless buttons onto a dummy plastic housing 500. One or more single push buttons 520A can be utilized to remotely initiate unrelated control functions for one or more devices. A plurality of wireless buttons 520B can be configured as a two dimensional mechanism that, for example, can function as a directional control much like a D-pad. Alternatively, a plurality of wireless buttons 520C can be configured to function in a manner similar to a slider-type mechanism, allowing for a level of a value to be easily increased or decreased.

Beyond the ability to establish remote control in a variety of locations for one or more devices that may otherwise not offer remote control capabilities, the present invention provides for many additional advantages. The wireless buttons can be configured to either function as a more permanent fixture, or be configured to be a temporary solution.

According to one embodiment, the wireless buttons could be configured to be disposable, for example, buttons comprising adhesive-backed membrane switches. Furthermore, the wireless buttons could be manufactured to be sterile, and thus capable of being placed within the sterile field found within an operating room. After a procedure, the buttons could be removed and discarded, thereby allowing the area to be easily cleaned. Possibility of contaminating the sterile field is also reduced since new buttons can be used in place of previously used buttons that would otherwise have to be sterilized.

Alternatively, the buttons could be built into a device, such as a mechanical shaver used in endoscopy. The advantage of such a design is that functional buttons can be added to the device without having to disrupt the casing of the device, thereby preventing any possibility of breaking a seal in the device in order to wire buttons from the external surface to the interior control points. The ability of the wireless buttons to provide a non-invasive electrical connection also eliminates costly changes to structures or devices in order to add control means.

Although the present invention has been described with reference to specific exemplary embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense.

What is claimed is:

1. A system for remotely controlling surgical devices, comprising:
    at least one wireless push button for providing a mechanical/electrical interaction to open or close a circuit upon physical touching or depressing of the push button by a user to operate one or more of the surgical devices disposed remotely therefrom;
    a sensor for wirelessly detecting the physical touching or depressing of said at least one wireless push button and outputting a wireless signal; and
    a central control unit for issuing operating signals to selectively operate one or more of the surgical devices in communication with the central control unit in response to receiving the wireless signal from the sensor that indicates activation of said at least one wireless push button,
    wherein said sensor is disposed at a location remote from said central control unit and remote from the surgical devices.

2. The system according to claim 1, wherein said wireless push button is disposed in a sterile field within an operating room and one of the surgical devices includes a handpiece that is energized by physical touching or depressing of the wireless push button by a user.

3. A system for remotely controlling one or more surgical devices in a medical or surgical environment, comprising:
    at least one surgical device;
    a central control unit connected to said at least one surgical device;
    at least one wireless button for controlling one or more functions of said at least one surgical device; and
    at least one portable sensor unit secured to an authorized user and separate from the wireless button for wirelessly detecting said at least one wireless button and for providing an output to said central control unit,
    wherein said central control unit receives the output from said at least one portable sensor unit and is configured for operatively controlling said at least one surgical device in response to the output and for preventing operation of said surgical device when an unauthorized user operates said wireless button.

4. The system according to claim 3, wherein said at least one wireless button comprises a disposable button disposed in a sterile field within an operating room, and wherein said at least one wireless button is separate from and disposed remotely from said at least one surgical device and said central control unit.

5. The system according to claim 3, wherein said at least one portable sensor unit that is secured to an authorized user comprises an RFID reader and said wireless button comprises an RFID tag, and wherein in response to a wireless signal from said RFID reader to said RFID tag, said RFID tag located in proximity to said RFID reader provides a return signal that comprises a control signal for the wireless button.

6. The system according to claim 3, wherein said at least one portable sensor unit is secured to a wrist of an authorized user, said portable sensor unit further comprising one of a finger cover disposed on a finger of an authorized user and a sticker disposed on a finger of an authorized user for securing an inductive coil to a finger of an authorized user, and comprising a wired connector connecting said inductive coil to said portable sensor unit.

7. The system according to claim 6, wherein said finger cover and said sticker are disposable devices for use in a sterile field of an operating room, and wherein said portable sensor unit comprises an RFID reader and said wireless button comprises an RFID tag.

8. The system of claim 3, comprising a sensor disposed at a location within an operating room to define an authorized area for wireless communication with said wireless button, wherein said wireless button provides a control signal read by said sensor when the wireless button is disposed within the authorized area, wherein said sensor provides the control signal to said central control unit so that said central control unit operates said at least one surgical device in response to receiving the output from said portable sensor unit and the control signal from said sensor.

9. The system of claim 3, wherein said at least one wireless button comprises a first button of a plurality of wireless buttons, and said at least one surgical device comprises one of a plurality of surgical devices in communication with said central control unit, wherein at least a second one of said wireless buttons operates a second one of said surgical devices.

10. The system of claim 9, wherein said plurality of wireless buttons comprise wireless push buttons, the system further comprising at least one medical device connected to said central control unit and controllable by a third one of said plurality of wireless push buttons.

11. A system for remotely controlling one or more devices in a medical or surgical environment, comprising:
    at least one surgical device;
    a central control unit connected to said at least one surgical device;
    at least one wireless button for controlling one or more functions of said at least one surgical device; and
    a sensor unit disposed at a location remote from said central control unit to define an activation area, said sensor unit for wirelessly detecting activation of said at least one wireless button and for providing an output to said central control unit,
    wherein said central control unit receives the output from said sensor unit when the wireless button is activated within the activation area and controls said at least one surgical device in response to the output from said at least one sensor unit, and wherein said sensor unit provides no output to said central control unit if the wireless button is activated away from the activation area.

12. The system according to claim 11, wherein said sensor unit comprises an inductive coil with a RFID reader and said wireless button comprises an RFID tag that normally is in an inoperative state, and said sensor unit is disposed at a location remote from said at least one surgical unit.

13. The system according to claim 11, wherein said sensor unit is disposed in an operating room ceiling to define an area of activation in an operating room.

14. The system according to claim 11, wherein said sensor unit comprises a sterilizable or initially sterile pad or sheet for placement on a table or surface near an area of interaction between the wireless button and a user.

15. The system according to claim 11, further comprising a portable sensor secured to the body of a user, wherein actuation of said wireless button provides a wireless control signal read by said portable sensor, and wherein said portable sensor outputs a wireless control signal to said central control unit so that said central control unit controls said at least one surgical device in response to the wireless control signal from said portable sensor and the output from said sensor unit.

16. The system of claim 11, further comprising a portable sensor mounted to the body of a user to define an authorized user, wherein said portable sensor receives a signal from said sensor unit and outputs a control signal to said sensor unit, wherein said sensor unit provides the output to said central control unit only when the sensor unit receives the output from said wireless button and the control signal from said portable sensor, and wherein said wireless button and said sensor unit are disposed at locations remote from said at least one surgical device.

17. The system of claim 11, wherein said at least one wireless button comprises a first button of a plurality of wireless buttons, and said at least one surgical device comprises one of a plurality of surgical devices in communication with said central control unit, wherein at least a second one of said wireless buttons operates a second one of said surgical devices.

18. The system of claim 17, wherein said plurality of wireless buttons comprise wireless push buttons, the system further comprising at least one medical device connected to said central control unit and controllable by a third one of said plurality of wireless push buttons.

19. The system of claim 3, wherein the system includes first and second surgical devices and the central control unit is connected to each said surgical device, and wherein the central control unit receives the output from said portable sensor unit to select one of the surgical devices and to operate the selected surgical device.

20. The system of claim 1, wherein one of the surgical devices includes a handpiece that is energized by the physical touching or depressing of the wireless push button.

21. The system of claim 1, wherein said at least one wireless push button is disposed remotely from the surgical devices and handpieces connected thereto, and wherein the surgical devices and the handpieces are free from wireless buttons.

* * * * *